United States Patent
DeVries et al.

(10) Patent No.: US 8,903,760 B2
(45) Date of Patent: Dec. 2, 2014

(54) METHOD AND SYSTEM FOR INFORMATION WORKFLOWS

(75) Inventors: James R. DeVries, Lincoln, NE (US); Saleem Hussain, Cambridge, MA (US); Cale T. Rath, Byron, MN (US); Saeid Sakhitab, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 3066 days.

(21) Appl. No.: 10/988,248

(22) Filed: Nov. 12, 2004

(65) Prior Publication Data
US 2006/0117238 A1    Jun. 1, 2006

(51) Int. Cl.
| | |
|---|---|
| G06F 7/00 | (2006.01) |
| G06F 17/30 | (2006.01) |
| G06F 19/00 | (2011.01) |
| G06Q 10/10 | (2012.01) |

(52) U.S. Cl.
CPC .............. *G06F 19/36* (2013.01); *G06F 19/322* (2013.01); *G06Q 10/10* (2013.01)
USPC ............................ 707/602; 707/728; 707/731

(58) Field of Classification Search
CPC .................... G06F 17/30563; G06F 17/30566; G06F 17/30569; G06F 17/30575; G06F 17/30283; G06F 17/30082; G06F 17/30861
See application file for complete search history.

(56) References Cited

U.S. PATENT DOCUMENTS

| | | | |
|---|---|---|---|
| 5,421,015 A * | 5/1995 | Khoyi et al. | 718/107 |
| 5,701,451 A | 12/1997 | Rogers et al. | |
| 5,805,970 A | 9/1998 | Kasamatsu | |
| 5,832,530 A | 11/1998 | Paknad et al. | |
| 5,917,828 A * | 6/1999 | Thompson | 370/474 |
| 5,937,392 A * | 8/1999 | Alberts | 705/14.52 |
| 5,948,062 A * | 9/1999 | Tzelnic et al. | 709/219 |
| 6,049,892 A * | 4/2000 | Casagrande et al. | 714/18 |
| 6,157,935 A * | 12/2000 | Tran et al. | 715/202 |
| 6,163,778 A | 12/2000 | Fogg et al. | |
| 6,167,439 A | 12/2000 | Levine et al. | |
| 6,185,598 B1 | 2/2001 | Farber et al. | |
| 6,199,068 B1 * | 3/2001 | Carpenter | 1/1 |
| 6,219,587 B1 * | 4/2001 | Ahlin et al. | 700/233 |
| 6,226,675 B1 * | 5/2001 | Meltzer et al. | 709/223 |
| 6,243,501 B1 | 6/2001 | Jamali | |
| 6,324,581 B1 * | 11/2001 | Xu et al. | 709/229 |
| 6,356,529 B1 | 3/2002 | Zarom | |
| 6,442,549 B1 | 8/2002 | Schneider | |
| 6,549,944 B1 | 4/2003 | Weinberg et al. | |
| 6,615,241 B1 * | 9/2003 | Miller et al. | 709/206 |

(Continued)

OTHER PUBLICATIONS

Chang et al. "Database machines and some issues on DBMS standards". IBM, May 19-22, 1980. pp. 191-2008.*

(Continued)

*Primary Examiner* — Daniel Kuddus
(74) *Attorney, Agent, or Firm* — Patterson & Sheridan LLP

(57) ABSTRACT

A method and apparatus for information repository workflows enables the transfer of information between healthcare sites and medical research facilities. Large quantities of medical information may be directly transferred to an information repository or indirectly transferred to the repository through the use of pointers. The information is cleansed and normalized prior to storage in a production database within the repository. The cleansing process is conducted while ensuring integrity of the production database is maintained and while continuing to receive additional information transfers. Errors encountered during processing are logged and reported.

23 Claims, 7 Drawing Sheets

(56) References Cited

U.S. PATENT DOCUMENTS

| | | | |
|---|---|---|---|
| 6,701,514 B1* | 3/2004 | Haswell et al. | 717/115 |
| 6,704,813 B2* | 3/2004 | Smirnov et al. | 710/52 |
| 6,708,189 B1* | 3/2004 | Fitzsimons et al. | 1/1 |
| 6,735,630 B1 | 5/2004 | Gelvin et al. | |
| 6,823,365 B1 | 11/2004 | Mattis et al. | |
| 6,839,751 B1* | 1/2005 | Dietz et al. | 709/224 |
| 6,939,751 B2* | 9/2005 | Zhu et al. | 438/151 |
| 6,970,939 B2* | 11/2005 | Sim | 709/236 |
| 6,983,478 B1* | 1/2006 | Grauch et al. | 725/13 |
| 6,993,657 B1* | 1/2006 | Renner et al. | 713/182 |
| 7,054,024 B2 | 5/2006 | Salgado et al. | |
| 7,062,723 B2 | 6/2006 | Smith et al. | |
| 7,120,865 B1 | 10/2006 | Horvitz et al. | |
| 7,143,033 B2 | 11/2006 | Belenger et al. | |
| 7,257,645 B2* | 8/2007 | Wiser et al. | 709/238 |
| 7,298,746 B1* | 11/2007 | De La Iglesia et al. | 370/394 |
| 7,333,514 B2* | 2/2008 | Anehem et al. | 370/474 |
| 7,386,438 B1 | 6/2008 | Franz et al. | |
| 7,437,364 B1 | 10/2008 | Fredricksen et al. | |
| 7,546,234 B1* | 6/2009 | Deb et al. | 704/9 |
| 7,546,284 B1* | 6/2009 | Martinez et al. | 1/1 |
| 7,568,151 B2 | 7/2009 | Bargeron et al. | |
| 7,593,961 B2 | 9/2009 | Eguchi et al. | |
| 7,844,666 B2 | 11/2010 | Horvitz et al. | |
| 2001/0037406 A1* | 11/2001 | Philbrick et al. | 709/250 |
| 2002/0031086 A1* | 3/2002 | Welin | 370/229 |
| 2002/0087704 A1* | 7/2002 | Chesnais et al. | 709/228 |
| 2002/0103811 A1* | 8/2002 | Fankhauser et al. | 707/104.1 |
| 2002/0156688 A1* | 10/2002 | Horn et al. | 705/26 |
| 2002/0169793 A1 | 11/2002 | Sweeney | |
| 2003/0046421 A1 | 3/2003 | Horvitz et al. | |
| 2003/0050821 A1 | 3/2003 | Brandt et al. | |
| 2003/0069881 A1 | 4/2003 | Huttunen | |
| 2003/0074248 A1* | 4/2003 | Braud et al. | 705/9 |
| 2003/0234956 A1 | 12/2003 | Salgado et al. | |
| 2004/0003352 A1 | 1/2004 | Bargeron et al. | |
| 2004/0064343 A1* | 4/2004 | Korpman et al. | 705/2 |
| 2004/0088646 A1* | 5/2004 | Yeager et al. | 715/500 |
| 2004/0193420 A1* | 9/2004 | Kennewick et al. | 704/257 |
| 2004/0215981 A1 | 10/2004 | Ricciardi et al. | |
| 2005/0060643 A1 | 3/2005 | Glass et al. | |
| 2006/0117238 A1 | 6/2006 | DeVries et al. | |
| 2012/0150962 A1 | 6/2012 | DeVries et al. | |

OTHER PUBLICATIONS

McGrory et al., "Communication of Medical Information Using Agents", ACM 2008.*

Cohen el at. "MAD Skills: New Analysis Practices for Big Data". ACM 2009.*

Brady et al. "eDiamond : a Grid-enabled federated database of annotated mammograms"; John Wiley & Sons, Ltd. 2002.*

Stanley et al., Database machine and some issues on DBMS standarads, Natinal Computer Conference, 1980.*

WO 2005/112390 A1, 2005; Vermeulen et al.*

Strother, Elizabeth, Denial of Service Protection: The Nozzle, Proceedings of the 16th Annual Computer Security Applications, Aug. 2000, IEEE Computer Society, Washington, United States.

Otto, Chris et al., System Architecture of a Wireless Body Area Sensor Network for Ubiquitous Health Monitoring, Journal of Mobile Multimedia, Jan. 2005, pp. 307-326, vol. 1, Issue 4, Rinton Press, Incorporated, Princeton, United States.

* cited by examiner

METHOD AND SYSTEM FOR INFORMATION
WORKFLOWS

BACKGROUND OF THE INVENTION

1. Field of the Invention

The present invention generally relates to the field of information transfer and storage and, more particularly, to a method and system for transferring large volumes of information from disparate or remote sites to central processing research facilities while allowing for the information to be cleansed and normalized prior to storage in a production data store.

2. Description of the Related Art

Advances in the area of clinical genomics have resulted in a desire to gather medical information in healthcare facilities and transfer the clinical data to medical research facilities for storage and analysis. The medical information for a patient may be gathered at different points in time and may vary from a small amount of data that can be easily transferred to large quantities of data that must also be accurately and securely transferred from a healthcare facility to a medical research facility.

Furthermore, the medical information for a patient may be represented using a variety of standards, each standard typically representing data of a specific type such as clinical documents, experimental data, clinical trial data, genomic data, and graphical data. To facilitate processing the medical information should be assembled in a standard format prior to storing the medical information in a production database located in a medical research facility. Currently, there is no known infrastructure to easily manage such assembly and storage.

Accordingly, there is a need for methods and systems for the secure transfer of varying quantities of data represented in a variety of standard formats from healthcare sites to medical research facilities.

SUMMARY OF THE INVENTION

The present invention generally is directed to methods and systems for moving medical information between healthcare sites and medical research facilities. Large quantities of medical information may be efficiently transferred, normalized, and cleansed prior to storage in a production data store.

One embodiment provides a method for transferring medical information between a healthcare domain and a production database within a research domain. A message including medical information or a link to a location storing the medical information is received by the research domain from the healthcare domain. The medical information is streamed into a datastore within the research domain. The medical information is then parsed to produce converted medical information prior to or while transferring the medical information from the datastore into a staging database within the research domain. Any ambiguities or errors in the converted medical information are identified prior to or while propagating the converted medical information from the staging database into the production database within the research domain.

Another embodiment provides a computer readable medium containing a program for processing medical information which, when executed, performs an operation of assembling and storing the medical information. The operation includes determining if a healthcare collaborative network (HCN) message includes a payload message or if the HCN message includes a pointer to a location where the payload message is stored. When the pointer is included within the HCN message the payload message is retrieved from the location. Once assembled, the payload message is stored in a datastore and parsed to produce a converted payload message represented in a standard database format. The converted payload message is streamed from the datastore into a staging database.

Still another embodiment provides a system for processing and storing medical information. The system includes an input unit, a shredding unit, and a cleansing unit. The input unit is configured to receive messages including medical information and stream the medical information to a datastore. The shredding unit is configured to parse the medical information to produce converted medical information while streaming the medical information from the datastore to a staging database. The cleansing unit configured to propagate the converted medical information from the staging database to a production database while identifying any ambiguities or errors in the converted medical information using a ruleset.

Still another embodiment provides a method for transferring data between a remote site and a production database within a central processing facility. A message generated by the remote site is received by the central processing facility. It is determined whether the data is included within the message or a pointer to a location where the data is stored is included within the message. When the pointer is included within the message the data is retrieved from the location. The data is stored in a datastore within the central processing facility and parsed to produce converted data represented in a standard relational database format. The converted data is streamed from the datastore into a staging database within the central processing facility.

Still another embodiment provides a method of preparing a document for transfer between a remote site and a central processing facility. It is determined whether the document exceeds a size threshold. When the document does not exceed the size threshold the document is combined with first header information to produce a message. When the document exceeds the size threshold a link to a location storing the document is generated and combined with second header information to produce the message.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENTS

Figure 1:
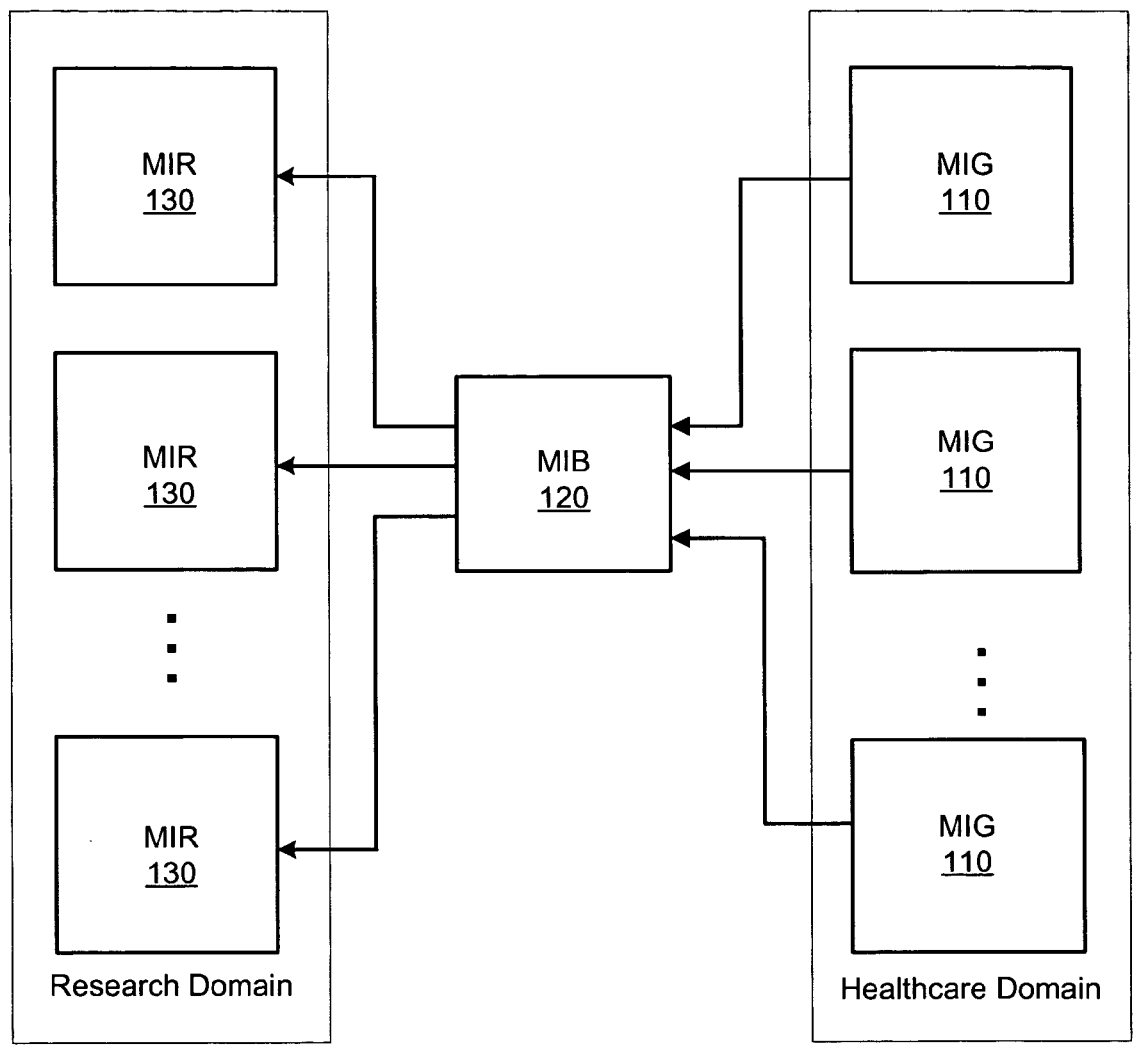
FIG. 1 is an exemplary medical information repository workflow environment according to one embodiment of the present invention.

The present invention provides methods and systems for the secure transfer of varying quantities of medical data represented in a variety of standard formats from healthcare sites to medical research facilities. The medical information is converted into a consistent format for storage in a production database. A workflow described herein permits continued transfer of new medical information during the processing of already received medical information. Furthermore, any errors detected during the processing are logged and reported.

While various embodiments of the present invention will be described in reference to medical information, those skilled in the art will recognize that the methods of transferring, assembling, and storing the medical information may be applied to other types of data. The methods and systems described herein are merely examples of specific applications of the present invention and although the present invention is described in the context of medical information it is not limited to one particular type of data.

In the following, reference is made to embodiments of the invention. However, it should be understood that the invention is not limited to specific described embodiments. Instead, any combination of the following features and elements, whether related to different embodiments or not, is contemplated to implement and practice the invention. Furthermore, in various embodiments the invention provides numerous advantages over the prior art. However, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

One embodiment of the invention is implemented as a program product for use with a computer system such as, for example, the medical information repository workflow environment shown in FIG. 1 and described below. The program (s) of the program product defines functions of the embodiments (including the methods described herein) and can be contained on a variety of signal-bearing media. Illustrative signal-bearing media include, but are not limited to: (i) information permanently stored on non-writable storage media (e.g., read-only memory devices within a computer such as CD-ROM disks readable by a CD-ROM drive); (ii) alterable information stored on writable storage media (e.g., floppy disks within a diskette drive or hard-disk drive); and (iii) information conveyed to a computer by a communications medium, such as through a computer or telephone network, including wireless communications. The latter embodiment specifically includes information downloaded from the Internet and other networks. Such signal-bearing media, when carrying computer-readable instructions that direct the functions of the present invention, represent embodiments of the present invention.

An Exemplary Infrastructure

FIG. 1 is an exemplary medical information repository workflow environment 100 according to one embodiment of the present invention. The medical information repository workflow environment 100 includes a healthcare domain and a research domain linked by a medical information broker (MIB) 120. The healthcare domain includes at least one medical information gateway (MIG) 110, typically located in a hospital, and the research domain includes at least one medical information repository (MIR) 130, typically located in a research facility. Medical information, such as clinical documents, experimental data, clinical trial data, genomic data, and graphical data may be generated or extracted by a hospital and submitted to the MIB 120 by a MIG 110. The MIB 120 then transfers the medical information, splitting the medical information into portions based on destination information provided by the MIG 110, to one or more MIRs 130 where it is processed and loaded into a production database. A MIR 130 receiving medical information from a MIG 110 may transfer messages, including error reports or logs to the MIG 110 via the MIB 120 following processing of the medical information. For some embodiments of the present invention, the medical information provided by the MIG 110 is represented in the form of an eXtensible markup language (XML) message and each XML message may contain multiple XML documents each of which is associated with a single patient. Alternatively, XML documents within an XML message may be associated with two or more patients.

Figure 2:
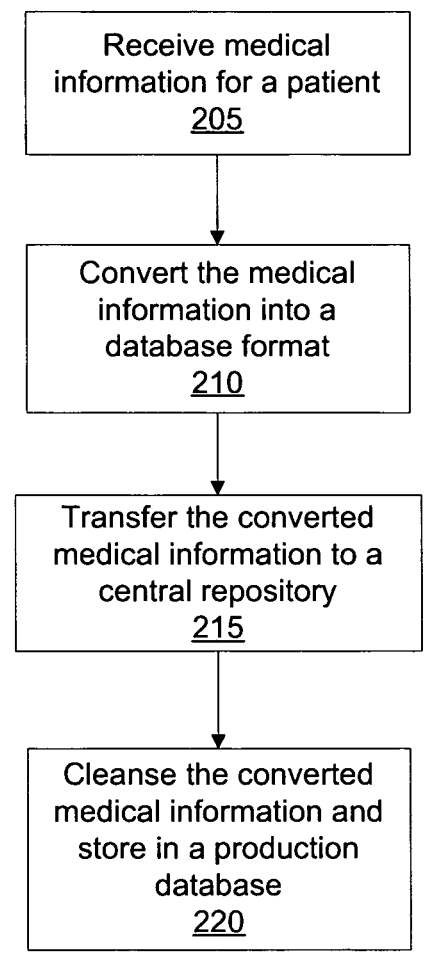
FIG. 2 is a flow diagram of an exemplary medical information repository workflow according to one embodiment of the present invention.

FIG. 2 is a flow diagram of an exemplary medical information repository workflow according to one embodiment of the present invention. In step 205 a MIG 110 receives medical information for one or more patients and transfers the medical information to a MIR 130 via the MIB 120, as described in conjunction with FIGS. 3 and 4. XML documents specifying the medical information may be specified in a variety of standard formats. For example, clinical document architecture (CDA) may be used for clinical documents such as discharge summaries and progress notes. Microarray gene expression markup language (MAGE-ML) may be used to specify microarray based experiment data. A vendor neutral and platform independent data format, such as operational data model (ODM) may be used to represent data collected in clinical trials. Genomic data may be represented using HapMap to specify patterns of human DNA sequences or bioinformatic sequence markup language (BSML) to specify biological sequence information, including graphical representations of sequences, genes, electrophoresis gels, multiple alignments, and the like.

In some embodiments of the present invention, the MIG 110 receiving the medical information de-identifies the information, as required by the health insurance portability and accountability act of 1996 (HIPAA) regulations, before transferring it to the MIB 120. Specific identification information associated with each patient is replaced with an encryption of the patient's identifying features called an anonymous global patient identifier (AGPI).

In step 210 the MIR 130 receives the medical information transferred from the MIG 110 through the MIB 120 and normalizes the medical information by converting the medical information represented in one or more formats into a standard XML database format to produce converted medical information. In some embodiments of the present invention, the MIR 130 uses an integrity checking technique, such as computing an MD5 checksum which is compared with a received checksum to determine that the medical information has been received without errors.

Figure 5:
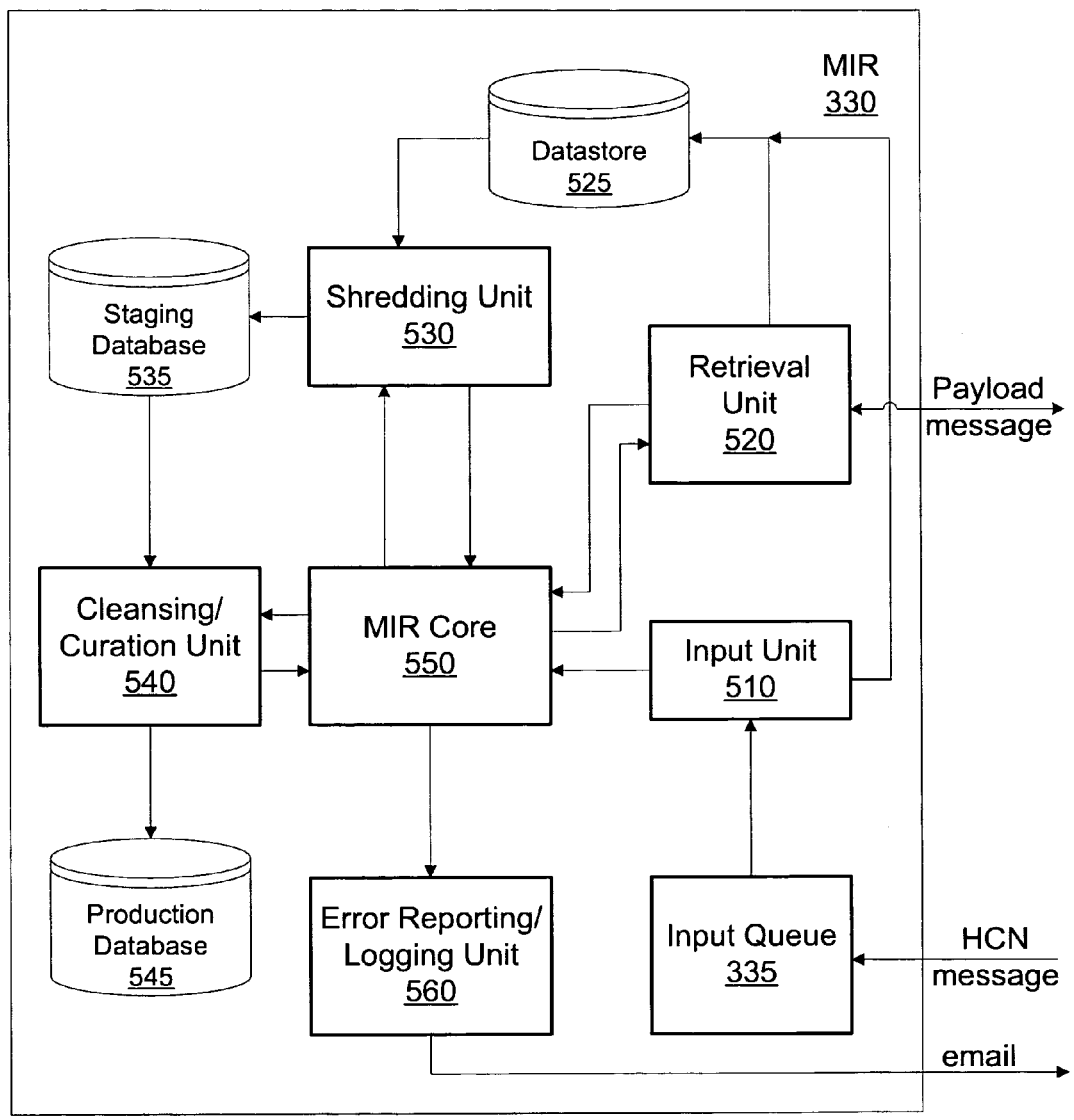
FIG. 5 is an exemplary medical information repository according to one embodiment of the present invention.
Figure 6:
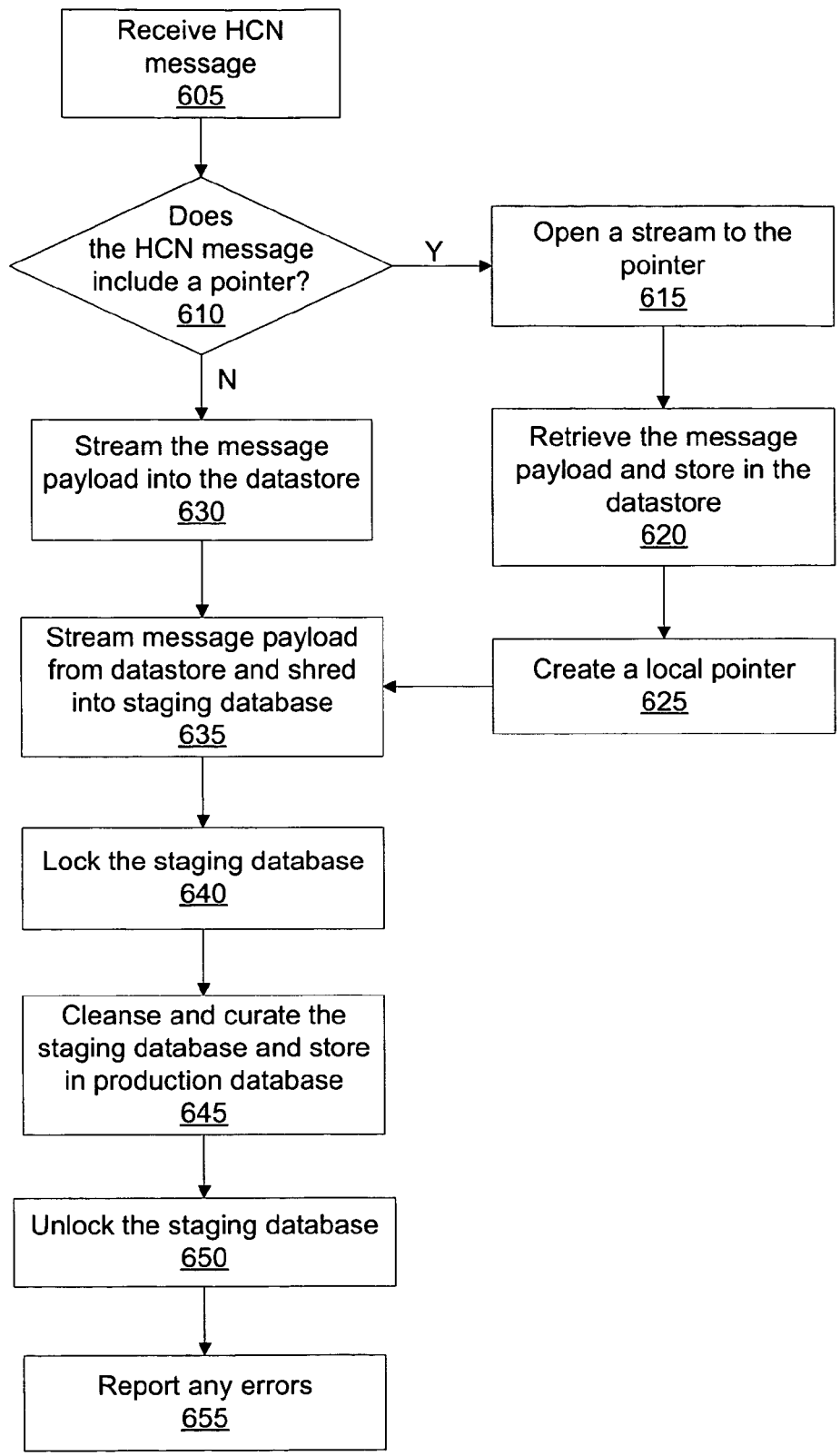
FIG. 6 is a flow diagram of an exemplary workflow for transferring and processing medical information according to one embodiment of the present invention.

In step 215 the converted medical information is transferred within the MIR 130 into a central repository, as described in conjunction with FIGS. 5 and 6. In step 220 the converted medical information is cleansed within the MIR 130 and stored in the production database. Data stored in the production database may be viewed using an appropriate data viewer, such as IBM's data discovery query builder (DDQB), and searched by researchers and physicians through the use of database access methods and mining tools, e.g., CGM-D, Spotfire, SAS, Fano, Genes@work, and the like. Persons skilled in the art will appreciate that any system configured to perform the method steps of FIG. 2, or their equivalents, is within the scope of the present invention.

Figure 3:
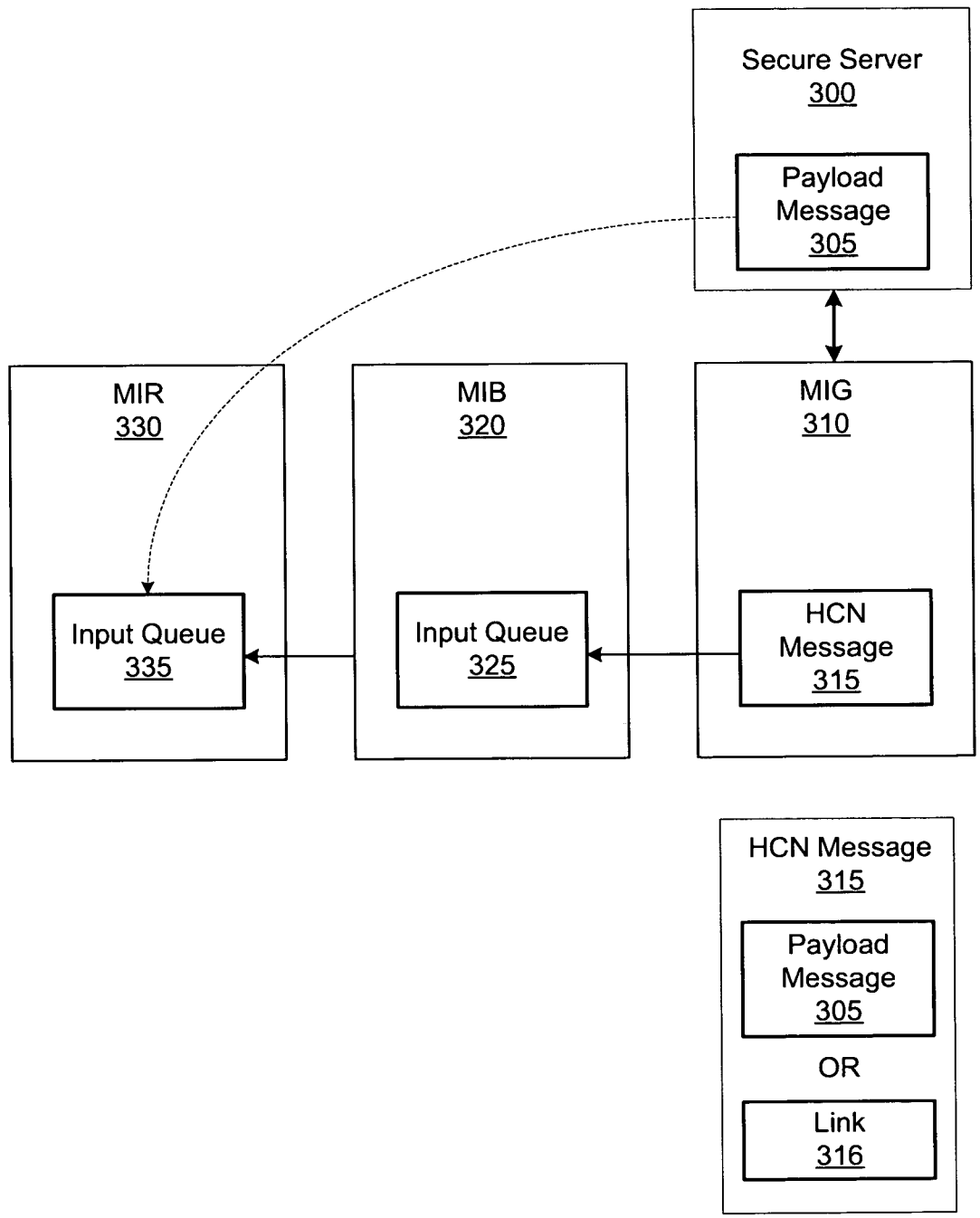
FIG. 3 is another exemplary medical information repository workflow environment according to one embodiment of the present invention.

FIG. 3 is another exemplary medical information repository workflow environment according to one embodiment of the present invention. The medical information may be represented by documents varying in size, including large documents that are several gigabytes or more in size, for example, documents containing genomic data. The MIG 310 is coupled to a secure server 300 storing a payload message 305 that includes the medical information. The secure server 300 may be any suitable type server capable of serving relatively large files, such as a hypertext transfer protocol (HTTP) server, a file transfer protocol (FTP) server, or network file server (NFS). In other embodiments of the present invention, the MIG 310 is coupled to additional secure servers 300. Each secure server 300 may be directly coupled to the MIG 310 or coupled to the MIG 310 via a network. In still other embodiments of the present invention, the payload message 305 is stored within the MIG 310.

When the payload message 305 is under a size threshold imposed by the message queuing system, the MIG 310 wraps payload message 305 with an outer message called a healthcare collaborative network (HCN) message to produce an HCN message 315 that is directly transmitted to a MIR 330. When the payload message 305 is too large to fit on a message queue, payload message 305 is indirectly transmitted to the MIR 330. Specifically, the HCN message 315 produced by the MIG 310 contains a uniform resource locator (URL) link 316 to the payload message 305 instead of the payload message 305. Therefore, medical information represented by smaller sized documents, such as those under 5 gigabytes, may be directly transmitted using a message input queue 325 within a MIB 320 and a message input queue 335 within the MIR 330. Larger payload messages are indirectly transmitted using the same message input queues to transmit the HCN message 315 containing the link 316.

Figure 4:
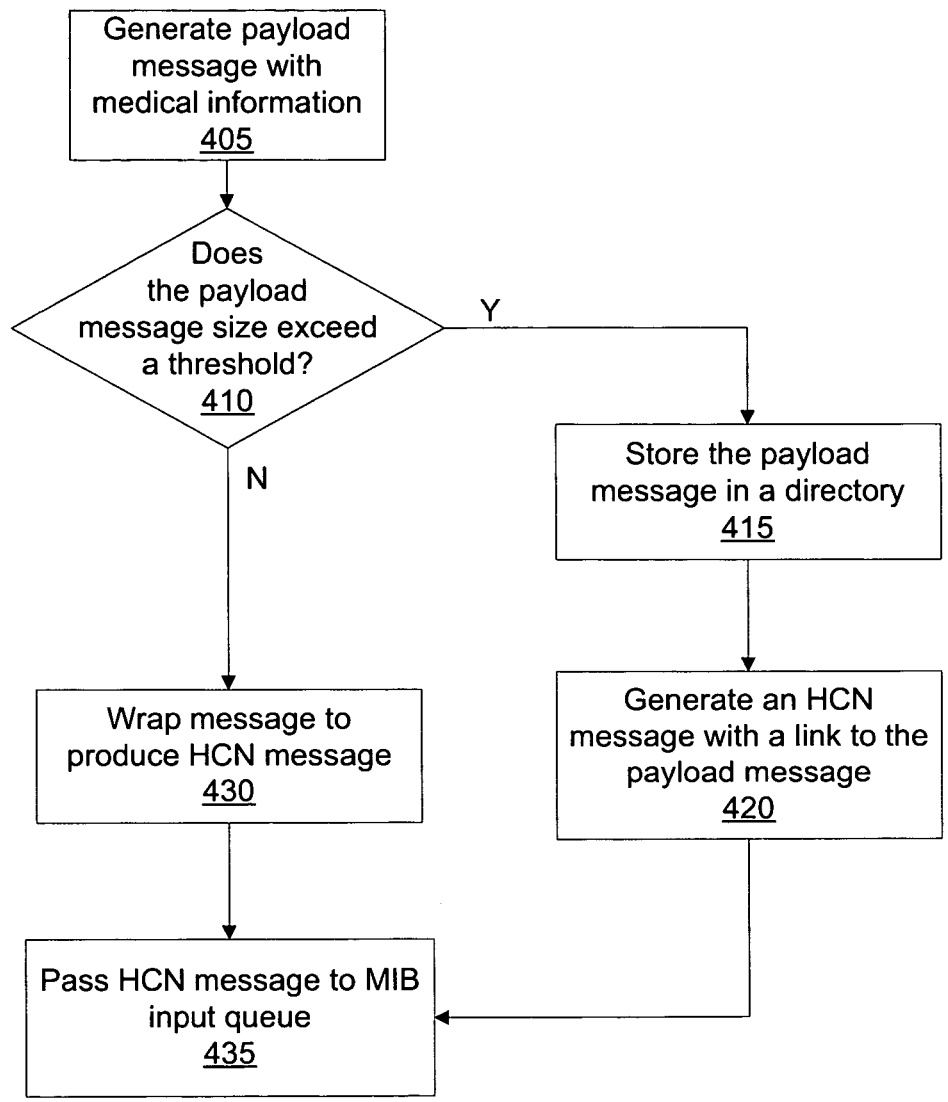
FIG. 4 is a flow diagram of an exemplary workflow for transferring varying quantities of medical information according to one embodiment of the present invention.

FIG. 4 is a flow diagram of an exemplary workflow for transferring varying quantities of medical information according to one embodiment of the present invention. In step 405 the MIG 310 generates a payload message including medical information, such as the payload message 305. The payload message 305 may include medical information for one or more patients and may include documents represented in varying standard formats. One or more data types and destination locations may be specified by metadata associated with the medical information. Such metadata may be included in a header within the HCN message. The code shown in Table 1 represents an exemplary payload message in XML format.

TABLE 1

```
<?xml version="1.0" encoding="UTF-8"?>
<sample_set>
  <sample lsid="urn:lsid:dcc.hapmap.org:Sample:NA12003:1">
  <from_individual
    lsid="urn:lsid:dcc.hapmap.org:Individual:CEPH1420.09:1" />
  <source>Coriell</source>
  <local_id>NA12003</local_id>
  </sample>
  <sample lsid="urn:lsid:dcc.hapmap.org:Sample:NA12004:1">
  <from_individual
    lsid="urn:lsid:dcc.hapmap.org:Individual:CEPH1420.10:1" />
  <source>Coriell</source>
  <local_id>NA12004</local_id>
  </sample>
</sample_set>
```

In step 410 MIG 310 determines if the size of the payload message 305 exceeds a threshold limit specified for message input queues 325 and 335. If, in step 410 the MIG 310 determines that the size of the payload message 305 does exceed the threshold limit, then in step 415, the MIG 310 stores the payload message in a directory, preferably located on a secure server, such as the secure Server 300. In step 420 the MIG 310 generates an HCN message, such as the HCN message 315 with the link 316 to the payload message 305 and proceeds to step 435. In some embodiments of the present invention, the HCN message 315 may include links to one or more secure servers, each server storing a portion of the payload message. A header within the HCN message may include metadata specifying one or more data types, routing information, or the like.

The code shown in Table 2 represents an exemplary HCN message in XML format including a link where the message mode is indicated as "link" and the standard format type is BSML. An MD5 checksum is included for verification of the transmission by the receiving MIR 330.

TABLE 2

```
<?xml version="1.0" encoding="UTF-8"?>
<HCN:HCN_Message>
<HCN:BrokerCommandRequest from="Cale's PC">
<HCN:Publish>
<HCN:PublishedData>
<HCN:TopicName>My topic</HCN:TopicName>
<HCN:PatientID>AH299837HD83792834764<HCN:PatientID>
<HCN:Timestamp>2003-03-03T17:45:35-08:00</HCN:Timestamp>
<HCN:XMLMessage mode="link">
   type="BSML"
   checksum="a61883f3b86a9a5114c61fadb1626ed1">
https://calerath.rchland.ibm.com/bsml_a345.xml
</HCN:XMLMessage>
</HCN:PublishedData>
</HCN:Publish>
</HCN:BrokerCommandRequest>
</HCN:HCN_Message>
```

In some embodiments of the present invention, a time range may be specified indicating the available time to download the payload message from the secure Server 300. The payload message may be deleted from the secure Server 300 after the time range has expired.

If, in step 410 the MIG 310 determines that the size of the payload message 305 does not exceed the threshold limit, then in step 430, the MIG 310 wraps the payload message 305 to produce the HCN message 315 and proceeds to step 435. The code shown in Table 3 represents an exemplary HCN message in XML format including a payload message (instead of a link).

TABLE 3

```
<?xml version="1.0" encoding="UTF-8"?>
<HCN:HCN_Message>
<HCN:BrokerCommandRequest from="Cale's PC">
<HCN:Publish>
<HCN:PublishedData>
<HCN:TopicName>My topic</HCN:TopicName>
<HCN:PatientID>AH299837HD83792834764<HCN:PatientID>
<HCN:Timestamp>2003-03-03T17:45:35-08:00</HCN:Timestamp>
<HCN:XMLMessage mode="embedded" type="BSML">
<![CDATA[
<sample_set>
<sample lsid="urn:lsid:dcc.hapmap.org:Sample:NA12003:1">
<from_individual
lsid="urn:lsid:dcc.hapmap.org:Individual:CEPH1420.09:1" />
<source>Coriell</source>
<local_id>NA12003</local_id>
</sample>
<sample lsid="urn:lsid:dcc.hapmap.org:Sample:NA12004:1">
<from_individual
lsid="urn:lsid:dcc.hapmap.org:Individual:CEPH1420.10:1" />
<source>Coriell</source>
<local_id>NA12004</local_id>
</sample>
</sample_set>
]]>
</HCN:XMLMessage>
</HCN:PublishedData>
</HCN:Publish>
</HCN:BrokerCommandRequest>
</HCN:HCN_Message>
```

In step 435 the MIG 310 passes the HCN message 315 (containing the payload message 305 or the link 316) to the input queue 325 within the MIB 320. The MIB 320 then routes the HCN message 315 to the input queue 335 within the MIR 330. The MIR 330 processes the HCN message 315 as described in conjunction with FIG. 6. Persons skilled in the art will appreciate that any system configured to perform the method steps of FIG. 4, or their equivalents, is within the scope of the present invention.

FIG. 5 is an exemplary MIR, such as the MIR 330, according to one embodiment of the present invention. The MIR 330 includes several workflow components, each of which may be placed on separate machines, permitting creation of a distributed environment for workflows that transport and transform medical information. Input queue 335 receives HCN messages directly or indirectly, each HCN message including medical information or a link thereto. The input unit 510 is an adapter or stub that reads the HCN messages from the input queue 335 and determines if an HCN message includes a payload message or a link to a payload message. The input unit 510 streams payload messages into a datastore 525 and forwards HCN messages that contain a link to the MIR core 550. In some embodiments of the present invention, the datastore 525 is a filesystem, relational database, or the like, that may be accessed by the workflow components within the MIR 330.

The MIR core 550 is the central workflow core and is responsible for directing the flow of incoming medical information represented as payload messages. The MIR core 550 forwards the link received from the input unit 510 to the retrieval unit 520 which attempts to retrieve the payload message stored at the location specified by the link. The payload message is streamed from a source location, such as the secure Server 300, directly to the filesystem, specifically to the datastore 525. Streaming the payload to the filesystem may be necessary because there may not be enough RAM on the system to contain the payload message, as the payload contained therein may be very large. Therefore, the size of input queue 335 may be reduced and payload messages that exceed the storage capacity of input queue 335 are indirectly transferred from a MIG to the MIR 330.

When the retrieval unit 520 is unable to retrieve the payload message, for any reason, such as an invalid link, non-responsive server, or the like, an error is reported to the MIR core 550. The MIR core 550 outputs all errors to an optional error reporting/logging unit 560 which communicates the error to the MIG providing the medical information. In some embodiments of the present invention, an email is sent to the MIG specifying the error. An error may be generated by the retrieval unit 520 or input unit 510 when the datastore 525 cannot store the incoming payload message. For example, space may not be available to store the incoming payload message or the datastore 525 may be unavailable.

In some embodiments of the present invention, the MIR core 550 generates a checksum, such as an MD5 checksum to validate the payload message in the datastore 525. If the checksum does not match the checksum received as part of the HCN message including the payload message, the MIR core 550 instructs the retrieval unit 520 to reattempt to download the payload message. The MIR core 550 generates an error, which is output to the error reporting/logging unit 560, when the checksums do not match following a reattempt at downloading the payload message.

A shredding unit 530 is responsible for "shredding" the medical information including data objects of varying formats. Shredding includes parsing the medical information specified in the payload message that is stored in the datastore 525 into the appropriate cells of a staging database 535, thereby producing converted medical information. One or more data types and destination locations may be specified by metadata associated with the medical information. The metadata is included in a header within the HCN message.

A cleansing/curation unit 540 is responsible for identifying ambiguities and errors from the converted medical information stored in the staging database 535 and propagating the converted medical information from the staging database 535 to the production database 545. For example, the cleansing/curation unit 540 may use a ruleset to determine whether or not data, such as blood pressure values, lies within a valid range and generate an error when a value outside of the valid range is encountered. Once the converted medical information is propagated from the staging database 535 to the production database 545 the converted medical information is accessible for queries and other database mining functions and it may be removed from the staging database 535. Any errors generated by the cleansing/curation unit 540 are output to the error reporting/logging unit 560 via the MIR core 550. Likewise, any errors generated by the shredding unit 530, such as invalid data types or destination locations, are also output to the error reporting/logging unit 560 via the MIR core 550. The cleansing/curation unit 540 may perform cleansing operations on the staging database 535 using a synchronous or asynchronous scheme, as described in conjunction with FIG. 7.

FIG. 6 is a flow diagram of an exemplary workflow for transferring and processing medical information according to one embodiment of the present invention. In step 605 the input queue 335 within the MIR 330 receives an HCN message containing either the payload message (medical information) or a link, i.e., pointer to the payload message. In step 610 the input unit 510 extracts a header from the HCN message. The header includes metadata which specifies whether the payload message is stored in the HCN message or is stored in another location, such as a remote secure server, and is available for download. In step 610 the input unit 510 also determines if the HCN message includes a pointer to the payload message, and, if so, in step 615 the input unit 510 passes the metadata to the MIR core 550. The MIR core 550 extracts a pointer from the metadata and passes the pointer to the retrieval unit 520.

In step 615 the retrieval unit 520 opens a stream to the payload message that the pointer references, where the pointer is the URL of the payload message. In some embodiments of the present invention, HTTP is used as the transport protocol for accessing remote payload messages. In step 620 the retrieval unit 520 accesses the payload message and streams it to the datastore 525. In step 625 the retrieval unit 520 creates a local pointer, e.g. URL, referencing the location of the payload message in the datastore 525. The local pointer should be small enough to be passed between the workflow components without degrading the performance of the MIR 330. The local pointer is passed by the retrieval unit 520 to the shredding unit 530 which proceeds to step 635.

If, in step 610 input unit 510 determines the HCN message does not include a pointer to the payload message, then, in step 630 the input unit 510 streams the payload message into the datastore 525, storing the payload message at a location specified by the metadata, and proceeds to step 635.

In step 635 the shredding unit 530 streams the payload message from the datastore 525 and shreds it into the staging database 535 and notifies the MIR core 550 that the payload message has been shredded to produce the converted payload message, i.e. converted medical information. In step 640 the cleansing/curation unit 540 is notified by the MIR core 550 that the converted payload message is in the staging database 535 and the MIR core 550 locks the staging database 535 so that it is not accessible by workflow components other than the cleansing/curation unit 540.

In step 645 the cleansing/curation unit 540 cleanses the converted payload message stored in the staging database, generating errors based on a defined ruleset, and propagates the converted payload message into the production database 545. The cleansing/curation unit 540 notifies the MIR core 550 that the cleansing operation is complete and outputs any errors that were generated during the cleansing operations to MIR core 550. In step 650 the MIR core 550 unlocks the staging database 535, permitting other workflow components access to the staging database 535. in step 655 the MIR core 550 outputs any errors generated by the cleansing/curation unit 540 to the error reporting/logging unit 560.

As described in conjunction with FIG. 6, the cleansing/curation unit 540 is instructed by MIR core 550 to perform the cleansing operation for each converted payload message as the converted payload message is available in the staging database 535. Therefore the cleansing is performed synchronously. In other embodiments of the present invention, the cleansing is performed asynchronously. Specifically, cleansing may be scheduled to be performed based on a trigger such as a specific time or when the space available for storing converted payload messages in the staging database 535 reaches a low water mark. Regardless of whether cleansing is performed synchronously or asynchronously the data stored in staging database 535 must remain consistent until the cleansing operation is complete.

Figure 7:
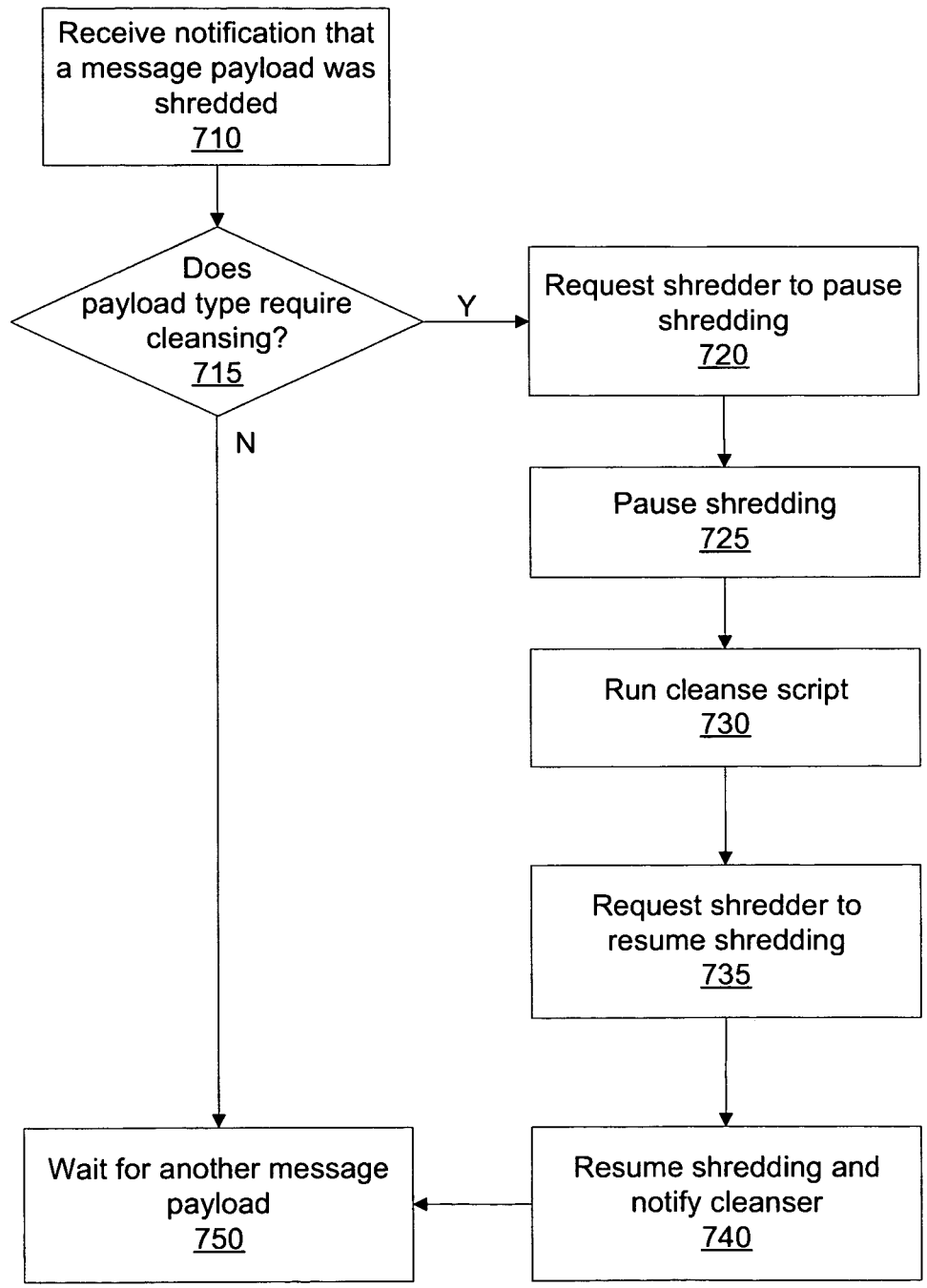
FIG. 7 is a flow diagram of an exemplary workflow for processing incoming messages while cleansing and curation operations are performed according to one embodiment of the present invention.

FIG. 7 is a flow diagram of an exemplary workflow for processing incoming payload messages while cleansing and curation operations are performed according to one embodiment of the present invention. In some embodiments of the present invention, steps 710 through 750 in FIG. 7 may replace steps 640, 645, and 650 in FIG. 6. The workflow for processing incoming payload messages may be used with either the synchronous or asynchronous cleansing scheme. Although, converted payload messages may not be added to staging database 535 during the cleansing operation, the overall workflow may continue processing incoming payload messages while holding off writes to the staging database 535 until the cleansing operation is complete.

In some embodiments of the present invention, the shredding unit 530 and the cleansing/curation unit 540 communicate with each other via queues. In step 710 the cleansing/curation unit 540 receives a notification from the shredding unit 530 that the converted payload message is available in the staging database 535. When the asynchronous scheme is used the notification is received by the cleansing/curation unit 540 when a trigger event occurs. Therefore, two or more converted payload messages may be stored in the staging database 535. In some embodiments of the present invention, the trigger event may occur independent of whether or not a converted payload message is stored in the staging database 535.

In step 710 the cleansing/curation unit 540 receives a notification that a converted payload message is in the staging database 535. In step 715 the cleansing curation unit 540 checks the converted payload message type and determines if the cleansing operation should be performed on the converted payload message. The determination of whether or not to perform the cleansing operation may be made based on a defined ruleset.

If, in step 715 the cleansing/curation unit 540 determines the cleansing operation should not be performed on the converted payload message, it proceeds to step 750. Otherwise, in step 720 the cleansing/curation unit 540 requests that the shredding unit 530 pause the shredding operation, thereby holding off any further writes to the staging database 535. In step 725 the shredding unit 530 completes the conversion of any payload message that is in progress and then pauses the shredding operation and notifies the cleansing/curation unit 540 that shredding is paused. In step 730 the cleansing/curation unit 540 receives the notification and runs a cleanse script to perform the cleansing operation. In some embodiments of the present invention, the cleanse script calls one or more cleansing applications.

In step 735 the cleansing/curation unit 540 completes the cleansing operation, i.e., the processing initiated by the cleanse script has completed, and the cleansing/curation unit 540 notifies the shredding unit 530 that shredding may resume. A command in the cleanse script may initiate notification of the shredding unit 530 or an application called by the cleanse script may initiate notification of the shredding unit 530. In step 740 the shredding unit 530 resumes the shredding operation and notifies the cleansing/curation unit 540 that shredding has resumed and proceeds to step 750. In step 750 the cleansing/curation unit 540 waits for another notification from the shredding unit 530 that a converted payload message is available in the staging database 535.

Persons skilled in the art will appreciate that any system configured to perform the method steps of FIGS. 6 and 7, or their equivalents, is within the scope of the present invention. The present invention provides methods and systems for medical information workflows to directly or indirectly transfer medical information represented in a variety of standard formats from healthcare sites to medical research facilities. The workflow permits continued transfer of medical information while the converted medical information stored in the staging database is cleansed and propagated to the production database. Furthermore, any errors detected the workflow components are logged and reported.

Finally, although FIGS. 2 and 4-6 refer to using the disclosed methodologies to assemble and store medical information, persons skilled in the art will understand that the disclosed methodologies may be applied to manage other types of data. Furthermore, although FIGS. 1, 3, and 5 refer to transferring medical information between a healthcare domain and a research domain, persons skilled in the art will understand that the disclosed methodologies may be used to transfer data between other remote sites and central processing facilities. The foregoing description and drawings are, accordingly, to be regarded in an illustrative rather than a restrictive sense.

While the foregoing is directed to embodiments of the present invention, other and further embodiments of the invention may be devised without departing from the basic scope thereof, and the scope thereof is determined by the claims that follow.

What is claimed is:

1. A computer implemented method for using a machine to transfer information between a first domain and a production database within a second domain, comprising:
   receiving, from a medical information broker system (MIB), a message including either a link to a location storing information from the first domain or a payload storing the information, wherein the information is specified in different formats, and wherein the message includes the link to the location storing the information when the stored information exceeds a threshold size; and
   in response to receiving the message:
      placing the message in an input queue,
      upon determining the message includes the link:
         streaming the information from the location, and
         storing the streamed information in a datastore within the second domain,
      upon determining the message includes the payload, storing the information from the payload in the datastore within the second domain,
      parsing the information by a machine to produce converted information represented in a single database format prior to or while transferring the information from the datastore into a staging database within the second domain, and
      upon determining that a ruleset requires cleansing of the converted information, identifying any ambiguities or errors in the converted information prior to or while propagating the converted information from the staging database into the production database within the second domain.

2. The method of claim 1, further comprising, reporting an error generated during the receiving of the message.

3. The method of claim 1, further comprising, reporting an error generated during the identifying.

4. The method of claim 1, further comprising, reporting an error generated during the parsing.

5. The method of claim 1, further comprising:
   locking access to the staging database to prevent any modification of the staging database prior to the identifying; and
   unlocking access to the staging database to allow modification of the staging database following the identifying.

6. The method of claim 1, wherein the identifying is initiated based on a trigger.

7. The method of claim 1, wherein the information includes an anonymous global patient identifier.

8. A non-transitory computer readable storage medium containing a program for processing medical information which, when executed by a machine, cause the machine to perform an operation, comprising:
   determining whether a payload message including the medical information is included within a healthcare collaborative network (HCN) message or a pointer to a location where the payload message is stored is included within the HCN message, and wherein the HCN message includes the pointer to the location storing the information when the payload message exceeds a threshold size, wherein the payload message is stored in an input queue;
   upon determining HCN message includes the pointer:
      retrieving the payload message from the location identified within the HCN message; and
      storing the retrieved information in a datastore;
   upon determining the HCN message includes the payload message, storing the information in the payload message in the datastore;
   parsing the payload message to produce a converted payload message represented in a standard database format;
   streaming the converted payload message from the datastore into a staging database; and
   upon determining that a ruleset requires cleansing of the converted information, identifying any ambiguities or errors in the converted payload message prior to or while propagating the converted payload message from the staging database to a production database.

9. The computer readable medium of claim 8, further comprising reporting errors generated during the retrieving of the payload message, the parsing of the payload message, and the identifying of any ambiguities or errors in the converted payload message.

10. The computer readable medium of claim 8, further comprising locking the staging database during the propagating of the converted payload message.

11. A computer implemented system including a machine for processing and storing information, comprising:
   an input unit configured to receive messages which include either a pointer to a location within a secure server where information is stored or a payload storing the information, wherein the information is specified in different formats, wherein the received messages include the link to the location within the secure server when a size of the information exceeds a threshold size, wherein the input unit stores payload messages in an input queue;
   a retrieval unit configured to retrieve the information corresponding to the received message from either the location within the secure server or from the payload and to stream the information to the datastore;
   a machine configured to, in response to receiving one of the message, parse the information to produce converted information represented in a single database format while streaming the information from the datastore to a staging database; and
   a cleansing unit configured to propagate the converted information from the staging database to a production database, wherein the cleansing unit identifies any ambiguities or errors in the converted information upon determining that a ruleset requires cleansing of the converted information.

12. The system of claim 11, wherein the cleansing unit is configured to generate an error when a portion of the information does not conform to a rule specified by the ruleset.

13. The system of claim 11, further comprising an information repository core configured to interface between the input unit and the machine and configured to interface between the machine and the cleansing unit.

14. The system of claim 11, further comprising an error reporting unit configured to receive errors generated by the input unit, the cleansing unit, or the machine.

15. The system of claim 11, wherein a core unit is configured to lock the machine while the cleansing unit cleanses the converted information and propagates the converted information to the production database.

16. The system of claim 11, wherein the cleansing unit initiates the cleansing of the converted information based on a trigger.

17. The system of claim 11, wherein the information includes an anonymous global patient identifier.

18. A computer implemented method for using a machine to transfer data between a remote site and a production database within a central processing facility, comprising:

receiving, from a medical information broker system (MIB), a message generated by the remote site that includes either a pointer to a location where data specified in different formats is stored or a payload storing data specified in different formats, and wherein the message includes the pointer to the location where the data is stored when a size of the data exceeds a threshold size; and in response to receiving the message:
placing the message in an input queue;
upon determining the message includes the pointer, retrieving the data from the location,
upon determining the message includes the payload, retrieving the data from the received message,
storing the data in a datastore within the central processing facility,
parsing the data by a machine to produce converted data represented in a standard relational database format,
streaming the converted data from the datastore into a staging database within the central processing facility; and
upon determining that a ruleset requires cleansing of the converted information, identifying any ambiguities or errors in the converted payload message prior to or while propagating the converted payload message from the staging database to a production database.

19. The method of claim 18, wherein the identifying is initiated based on a trigger.

20. The method of claim 18, further comprising, reporting an error generated during the retrieving of the data.

21. The method of claim 18, further comprising, reporting an error generated during the parsing.

22. The method of claim 18, further comprising:
locking access to the staging database to prevent any modification of the staging database prior to the identifying; and
unlocking access to the staging database to allow modification of the staging database following the identifying.

23. The method of claim 18, wherein the information includes an anonymous global patient identifier.

* * * * *